(12) United States Patent
Biniazan et al.

(10) Patent No.: US 12,702,373 B2
(45) Date of Patent: Aug. 11, 2026

(54) PROVIDING A COMPLETE SET OF SECOND KEY ELEMENTS IN AN X-RAY IMAGE

(71) Applicant: Siemens Healthcare GmbH, Erlangen (DE)

(72) Inventors: Ramyar Biniazan, Nuremberg (DE); Steffen Kappler, Effeltrich (DE); Ludwig Ritschl, Buttenheim (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 459 days.

(21) Appl. No.: 18/152,381

(22) Filed: Jan. 10, 2023

(65) Prior Publication Data

US 2023/0233169 A1 Jul. 27, 2023

(30) Foreign Application Priority Data

Jan. 13, 2022 (EP) .................................... 22151400

(51) Int. Cl.
*A61B 6/00* (2006.01)
*G06T 7/00* (2017.01)

(52) U.S. Cl.
CPC .............. *A61B 6/52* (2013.01); *G06T 7/0012* (2013.01); *G06T 2207/10116* (2013.01); (Continued)

(58) Field of Classification Search
CPC ......... G06T 7/0014; G06T 2207/20081; G06T 2207/20084; G06T 2207/30061; G06T 7/73; G06T 7/0012; G06T 2207/10116–10128; G06T 7/11; G06T 9/002; G06T 5/60; A61B 6/5247; (Continued)

(56) References Cited

U.S. PATENT DOCUMENTS 10,849,585 B1 12/2020 Teixeira et al.
2016/0361035 A1 12/2016 Lee et al.
(Continued)

FOREIGN PATENT DOCUMENTS

CN 112262410 A 1/2021
CN 112313715 A 2/2021
(Continued)

*Primary Examiner* — Atiba O Fitzpatrick
(74) *Attorney, Agent, or Firm* — Harness, Dickey & Pierce, P.L.C.

(57) ABSTRACT

A method comprises: applying a first trained function to first input data to generate first output data, the first output data including first key elements; receiving second input data, the second input data being an X-ray image of an examination region acquired using a first collimation region; applying a second trained function to the second input data to generate second output data, the second output data including second key elements; receiving third input data in response to an incomplete set of second key elements, the third input data including the second key elements and an X-ray image of the examination region acquired using the first collimation region; applying a third trained function to the third input data to generate third output data, the third output data including an estimated third key element to complete the set of second key elements; and providing a complete set of second key elements.

15 Claims, 6 Drawing Sheets

(52) U.S. Cl.
CPC ............... *G06T 2207/20081* (2013.01); *G06T 2207/30004* (2013.01); *G06T 2207/30168* (2013.01); *G06T 2207/30204* (2013.01)

(58) Field of Classification Search
CPC ... A61B 5/0077; A61B 5/7267; A61B 5/0035; A61B 6/5211; A61B 6/469; A61B 6/06; G06N 3/0464; G06N 3/084; G06N 3/08; G06N 3/02–126; G06N 20/00–20; G06V 10/25; G06V 10/44; G06V 10/764; G06V 10/82; G06V 10/70; G06V 10/774–7796; G06V 10/454; G21K 1/02–046; G01N 2223/316; G01N 29/4481; A61N 5/1045; G06K 9/6256; G06K 9/6257; G06K 9/6259; G06F 18/214–2155; G06F 7/023; G06F 40/16
See application file for complete search history.

(56) References Cited

U.S. PATENT DOCUMENTS

2018/0071452 A1 3/2018 Sharma et al.
2018/0338742 A1* 11/2018 Singh .................... A61B 6/587
2019/0069871 A1* 3/2019 Tkaczyk .............. A61B 6/4452
2020/0000425 A1 1/2020 Ji et al.
2020/0008768 A1 1/2020 Young et al.
2020/0058389 A1* 2/2020 Saalbach ................ A61B 6/544
2020/0250824 A1 8/2020 Yi et al.
2020/0305821 A1 10/2020 Sendai
2020/0311869 A1* 10/2020 Reaungamornrat .. G06T 3/4046
2020/0312478 A1 10/2020 Sutter
2020/0410670 A1* 12/2020 Gerard .................... G06T 7/143
2021/0093284 A1 4/2021 Sutter et al.
2021/0110584 A1 4/2021 Claessen et al.
2021/0192727 A1 6/2021 Ward et al.
2021/0312659 A1 10/2021 Sommer et al.
2021/0358119 A1 11/2021 Vahala
2022/0277835 A1* 9/2022 Senegas ............... A61B 6/5247
2022/0287664 A1 9/2022 Taki
2024/0298995 A1* 9/2024 Flexman ................ A61B 6/467

FOREIGN PATENT DOCUMENTS

EP 3135201 A1 3/2017
EP 3689241 A1 8/2020
EP 3718481 A1 10/2020

* cited by examiner

10
Receive first input data
11
Apply first trained function to first input data
12
Receive second input data
13
Apply second trained function to second input data
14
Check second key elements
15
Receive third input data
16
Apply third trained function to third input data
17
Provide final output data
18

10
21
22
23
24
25
+/−
26
27
28
29
30
31
No
Yes
32
33
34
250
260
261, 262,
263, 264, 265
270
271, 272,
273, 274
280
281
282
283

100
110
111
112
113
120
121
122
123
124
125
126
127
128
129
130
131
132
140
141
142

200
210
211
212
212
213
214
220
221
222
223

PROVIDING A COMPLETE SET OF SECOND KEY ELEMENTS IN AN X-RAY IMAGE

CROSS-REFERENCE TO RELATED APPLICATION(S)

The present application claims priority under 35 U.S.C. § 119 to European Patent Application No. 22151400.3, filed Jan. 13, 2022, the entire contents of which are incorporated herein by reference.

FIELD

One or more example embodiments of the present invention relate to a computer-implemented method for providing a complete set of second key elements in an X-ray image, a computer-implemented method for providing a trained function, a providing system, a computer program product, a computer-readable medium, a training system, a computer program product, a computer-readable medium, and an X-ray system, wherein an automatic collimation based on an optical image is improved.

BACKGROUND

An X-ray system, e.g. a radiography system or a fluoroscopy system, comprises an X-ray source and an X-ray detector. The examination object, in particular a patient, is arranged between the X-ray source and the X-ray detector so that an X-ray image of an examination region can be acquired. The X-ray beam of the X-ray source is limited by a collimator. The collimator defines a collimation region. A typical shape of the collimation region is a rectangular shape delimited on four sides by collimator blades. Within the collimation region, X-rays penetrate the examination object and the X-rays, which penetrated the object, are detected by the X-ray detector.

One known technique to define collimator borders or the collimation region is to use an RGB camera together with a depth camera, or a 3D camera. The camera in the acquisition room would first capture an image from the patient or examination object. A couple of key elements can be identified on the image, e.g. by using an AI model. The key elements can be used to define the collimator borders or the collimation region.

Auto-collimation techniques are a necessary part in acquiring X-ray images. Collimators are devices used to restrict and narrow beams which define the border of the X-ray image. Well-chosen collimator settings or a well-chosen collimation region are one of the crucial aspects of improving the radiographic imaging technique. The well-chosen collimation region prevents unnecessary exposure outside the region of interest. Further, the well-chosen collimation region improves the image quality by producing less scatter radiation, e.g. generated outside the region of interest. The region of interest, e.g. the lung, lies within an examination region.

However, it might be possible that some necessary parts of the organ to be imaged is not shown in its entirety in the X-ray image due to a faulty setting of the collimation region. E.g. the collimation region is not large enough to image the organ in total.

SUMMARY

It is an object of one or more example embodiments of the present invention to provide a computer-implemented method for providing a complete set of second key elements in an X-ray image, a computer-implemented method for providing a trained function, a providing system, a computer program product, a computer-readable medium, a training system, a computer program product, a computer-readable medium, and an X-ray system, which reduce the need for retakes of X-ray images.

The object of one or more example embodiments of the present invention is solved by a computer-implemented method for providing a complete set of second key elements in an X-ray image, a computer-implemented method for providing a trained function, a providing system, a non-transitory computer program product, a non-transitory computer-readable medium, a training system, a non-transitory computer program product, a non-transitory computer-readable medium, and an X-ray system, according to one or more example embodiments of the present invention.

In the following, a solution according to one or more example embodiments of the present invention is described with respect to the claimed providing systems as well as with respect to the claimed methods. Features, advantages or alternative embodiments herein can be assigned to the other claimed objects and vice versa. In other words, claims for the providing systems can be improved with features described or claimed in the context of the methods. In this case, the functional features of the method are embodied by objective units of the providing system.

Furthermore, in the following, the solution according to one or more example embodiments of the present invention is described with respect to methods and systems for providing complete set of second key elements in an X-ray image as well as with respect to methods and systems for the training of the trained function. Features, advantages or alternative embodiments herein can be assigned to the other claimed objects and vice versa. In other words, claims for methods and systems for training of the trained function can be improved with features described or claimed in context of the methods and systems for providing complete set of second key elements in an X-ray image, and vice versa.

In particular, the trained function of the methods and systems for providing complete set of second key elements in an X-ray image can be adapted by the methods and systems for training of the trained function. Furthermore, the input data can comprise advantageous features and embodiments of the training input data, and vice versa. Furthermore, the output data can comprise advantageous features and embodiments of the output training data, and vice versa.

One or more example embodiments of the present invention relate to a computer-implemented method for a complete set of second key elements in an X-ray image, comprising:

- receiving first input data, in particular with a first interface, wherein the first input data is an optical image of an examination region,
- applying a first trained function to the first input data, in particular with a computation unit, wherein first output data is generated, wherein the first output data comprises detected first key elements and a first collimation region is determined based on the first key elements,
- receiving second input data, in particular with a second interface, wherein the second input data is an X-ray image of an examination region, acquired using the first collimation region,
- applying a second trained function to the second input data, in particular with a first computation unit, wherein second output data is generated, wherein the second output data comprises detected second key elements, checking a set of second key elements for completeness, in case of an incomplete set of second key elements:

receiving third input data, in particular with a third interface, wherein the third input data comprises an x-ray image of an examination region acquired using the first collimation region, and the second key elements, applying a third trained function to the third input data, in particular with a computation unit, wherein third output data is generated, wherein the third output data comprises at least one estimated third key element to complete the set of second key elements, providing final output data, in particular with a fourth interface, comprising a complete set of second key elements.

One or more example embodiments of the present invention can be applied for various X-ray systems, especially radiography systems, mammography systems, or fluoroscopy systems. The X-ray system can comprise a camera, in particular a 3D camera, an X-ray source, and an X-ray detector. In this invention, the example of a chest X-ray image is considered to explain the present invention. One or more example embodiments of the present invention can be applied to other anatomical regions of the body. The key elements, in particular number and location, can differ from body region to body region.

A key element can describe a position or a coordinate of a relevant anatomical feature, e.g. lung border, bone, joint etc. The key element can be a point, a line, an area, or a volume. In a preferred embodiment, the key element can be a point, also called a key point. In another embodiment, the key element can be a line, e.g. describing the border of a bone. The key element can comprise a shape, e.g. point, line, area, or volume, and a position. The position can be defined for example by the center of the shape. The key element and, preferably, a set of key elements can describe an anatomical feature and/or its position.

The first input data is an optical image of an examination region. The term “optical” can describe that an optical device and/or optical means were used for the acquisition of the optical image. A 2D or 3D camera can be used to acquire the optical image. The optical device can use a wavelength from 380 nm to 780 nm. The optical image can comprise color information, in particular RGB information, of the examination region. The optical image can comprise depth information of the examination region. In a preferred embodiment, the optical image comprises RGB information and depth information. In another embodiment, the optical image comprises RGB information only or depth information only. In a use case in the field of mammography, the optical image can comprise depth information only. A depth camera can be used.

A first trained function, in particular a deep learning algorithm, is applied to the first input data, wherein first output data is generated. The first output data comprises detected first key elements in the optical image. A first collimation region is determined based on the first key elements. The first collimation region can be calculated or computed based on the first key elements. The first key elements are detected in the optical image. Key elements can be defined as characteristic features within the examination region. Image recognition algorithms, pattern recognition algorithms or other image processing algorithms can be used to detect the key elements. Especially, the first trained function can be based on a machine learning algorithm or deep learning algorithm.

The second input data is an X-ray image of an examination region, acquired using the first collimation region. A second trained function is applied to the second input data wherein second output data is generated. The second trained function can be based on a machine learning algorithm or a deep learning algorithm. The second output data comprises detected second key elements in the X-ray image. A set of key elements can comprise all detected second key elements. The X-ray image can correspond to a first collimation region.

In a next step, a set of second key elements is checked for completeness. A certain number of key elements is required for setting the collimation region. For example, four key elements can be used to set a rectangular shaped collimation region.

In case of an incomplete set of second key elements, third input data is received. The third input data comprises an x-ray image of an examination region acquired using the first collimation region, and the second key elements. A third trained function is applied to the third input data wherein third output data is generated. The third trained function can be based on a machine learning algorithm or a deep learning algorithm. The third output data comprises at least one estimated third key element to complete the set of second key elements.

Final output data is provided which comprises a complete set of second key elements. The complete set of second key elements can comprise the at least one estimated third key element.

According to an aspect of one or more example embodiments of the present invention, the complete set of second key elements is transferred to the optical image. A second key element can be transferred via image registration techniques to the optical image. The key element is chosen in such a way that the key element can be detected in the optical image as well as in the X-ray image. A mapping of a second key element in the X-ray image and a first key element in the optical image can be carried out.

According to an aspect of one or more example embodiments of the present invention, a second collimation region is determined based on the transferred complete set of second key elements. The second collimation region can be used for the re-take of the X-ray image.

According to an aspect of one or more example embodiments of the present invention, a second X-ray image of the examination region is acquired using the second collimation region. The second X-ray image can correspond to a second collimation region.

The general concept of one or more example embodiments of the present invention is based on using an X-ray image to create a feedback loop to check whether the collimation region was correct. The first collimation region with its borders is defined by the optical image, in particular an RGB image in combination with a depth image. The first collimation region is used to acquire the (first) X-ray image, e.g. of the chest.

This X-ray image will be processed by the second trained function, in particular embodied as an AI model, to detect key elements which are relevant to those detected in the optical image by the first trained function which can be called a RGB/depth key elements model. In case of at least one missing key element in the X-ray image, the third trained function will be used to estimate the position of the at least one missing key element. It is clear that the at least one missing key element should be located somewhere outside of the image. The third trained function can estimate or predict the location of the at least one missing key element, also called the at least one third key element.

After estimating the at least one third key element, the at least one third key element and the detected second key elements form a complete set of second key elements. The complete set of second key elements in coordinates of the X-ray image can be mapped, e.g. by using an image registration technique, to the optical image. In doing so, the location of the at least one third key element can be determined in the optical image. In a subsequent step, a second collimation region can be computed or calculated based on the complete set of second key elements, which are now available in coordinates of the optical image, based on the optical image.

A second X-ray image can be acquired using the second collimation region. The second X-ray image can be used again as second input data in order to determine second key elements in the second X-ray image by applying the second trained function. If all second key elements are found in the second X-ray image, the second X-ray image can be used for further steps, e.g. diagnosis by a radiologist. If at least one second key element is missing again, the procedure of estimating the at least one third key element is repeated, and a third collimation region can be calculated. The method can be used in an iterative way in order to get an X-ray image with a complete set of second key elements. An X-ray image with a complete set of second key elements is considered as complete X-ray image of the examination region or region of interest. An X-ray image with an incomplete set of second key elements is considered as incomplete X-ray image of the examination region or region of interest. The incomplete X-ray image can be considered as a cropped X-ray image in which details of the region of interest are missing.

According to an aspect of one or more example embodiments of the present invention, the choice of the key elements as such should consider that the key elements are definable both in the optical image and the X-ray image. The key element can be defined at the location of a body part, e.g. a shoulder, or a structural feature of the body, e.g. a bone. In a preferred embodiment, the key elements can be defined by the user. In another embodiment, a set of key elements can be defined for a region of interest or an examination region. As an example, for a chest X-ray image four key elements can be defined which can be located at four corners of a rectangle. The collimation region can be determined based on the first key elements. The first key elements can be located within the collimation region, e.g. with a certain distance to the border of the collimation region.

One or more example embodiments of the present invention allow the use of the X-ray image to correct a possible collimation error which can be caused by determining the collimation region based on the optical image, especially using the first trained function. Furthermore, X-ray images can be checked repeatedly to make sure all necessary key elements are available. In case of missing key elements, the procedure would be repeated to define a new collimation region.

One or more example embodiments of the present invention further relate to a computer-implemented method for providing a third trained function, comprising:

- receiving input training data, in particular with a first training interface, wherein the input training data comprises an X-ray image corresponding to the first collimation region,
- receiving output training data, in particular with a second training interface, wherein the output training data is related to the input training data, wherein the output training data comprises at least one estimated third key element,
- training a third function based on the input training data and the output training data, in particular with a training computation unit,
- providing the third trained function, in particular with a third training interface.

The input training data comprises an X-ray image acquired using the first collimation region. The X-ray image can correspond to the first collimation region. The output training data is related to the input training data, wherein the output training data comprises the at least one third key element. In a preferred embodiment, the complete X-ray image can form the basis for the input training data and the output training data. A second collimation region can be determined based on the complete X-ray image. The border or outline of the complete X-ray image can be used for defining the second collimation region and/or the at least one third key element. A collimation region in general can be defined by an outline or a border of an area. For the input training data, the X-ray image is used. This X-ray image can be a cropped version of the complete X-ray image, e.g. the complete X-ray image can be cropped or cut off at one side. The border or outline of the X-ray image can be used for defining the collimation region. Therefore, the input training data and the output training data are related and a ground truth is available for the training.

In a preferred embodiment, the third trained function can be based on a deep learning method. In general, a trained function mimics cognitive functions that humans associate with other human minds. In particular, by training based on training data the trained function is able to adapt to new circumstances and to detect and extrapolate patterns.

In general, parameters of a trained function can be adapted via training. In particular, supervised training, semi-supervised training, unsupervised training, reinforcement learning and/or active learning can be used. Furthermore, representation learning (an alternative term is "feature learning") can be used. In particular, the parameters of the trained functions can be adapted iteratively by several steps of training.

In particular, a trained function can comprise a neural network, a support vector machine, a decision tree and/or a Bayesian network, and/or the trained function can be based on k-means clustering, Q-learning, genetic algorithms and/or association rules. In particular, a neural network can be a deep neural network, a convolutional neural network or a convolutional deep neural network. Furthermore, a neural network can be an adversarial network, a deep adversarial network and/or a generative adversarial network.

According to an aspect of one or more example embodiments of the present invention the at least one estimated third key element is deduced from a complete X-ray image. According to an aspect of one or more example embodiments of the present invention, the input training data is based on a cropped X-ray image of the complete X-ray image.

One or more example embodiments of the present invention further relate to a method for providing a complete set of second key elements in an X-ray image, wherein the trained function was provided by the method for providing the trained function.

One or more example embodiments of the present invention further relate to a providing system, comprising a first interface, configured for receiving first input data, wherein the first input data is an optical image of an examination region,

- a first computation unit, configured for applying a first trained function to the first input data, wherein first output data is generated, wherein the first output data comprises detected first key elements and a first collimation region is determined based on the first key elements,
- a second interface, configured for receiving second input data, wherein the second input data is an X-ray image of an examination region, acquired using the first collimation region,
- a second computation unit, configured for applying a second trained function to the second input data, wherein second output data is generated, wherein the second output data comprises detected second key elements,
- a checking unit, configured for checking a set of second key elements for completeness, in case of an incomplete set of second key elements:
- a third interface, configured for receiving third input data, wherein the third input data comprises an x-ray image of an examination region acquired using the first collimation region, and the second key elements,
- a third computation unit, configured for applying a third trained function to the third input data, wherein third output data is generated, wherein the third output data comprises at least one estimated third key element to complete the set of second key elements,
- a fourth interface, configured for providing final output data, comprising a complete set of second key elements.

One or more example embodiments of the present invention further relate to a computer program product comprising instructions which, when the program is executed by a providing system, cause the providing system to carry out the method for providing a complete set of second key elements in an X-ray image.

One or more example embodiments of the present invention further relate to a computer-readable medium comprising instructions which, when executed by a providing system, cause the providing system to carry out the method for providing a complete set of second key elements in an X-ray image.

One or more example embodiments of the present invention further relate to a training system, comprising:

- a first training interface, configured for receiving input training data, wherein the input training data comprises an X-ray image corresponding to the first collimation region,
- a second training interface, configured for receiving output training data, wherein the output training data is related to the input training data, wherein the output training data comprises at least one estimated third key element,
- a training computation unit, configured for training a third function based on the input training data and the output training data,
- a third training interface, configured for providing the third trained function.

One or more example embodiments of the present invention further relate to a computer program product comprising instructions which, when the program is executed by a training system, cause the training system to carry out the method of providing a trained function.

One or more example embodiments of the present invention further relate to a computer-readable medium comprising instructions which, when executed by a training system, cause the training system to carry out the method of providing a trained function.

One or more example embodiments of the present invention further relate to an X-ray system comprising the providing system.

BRIEF DESCRIPTION OF THE DRAWINGS

Examples of embodiments of the present invention are explained in more detail below with regard to the drawings.

DETAILED DESCRIPTION

Figure 1:
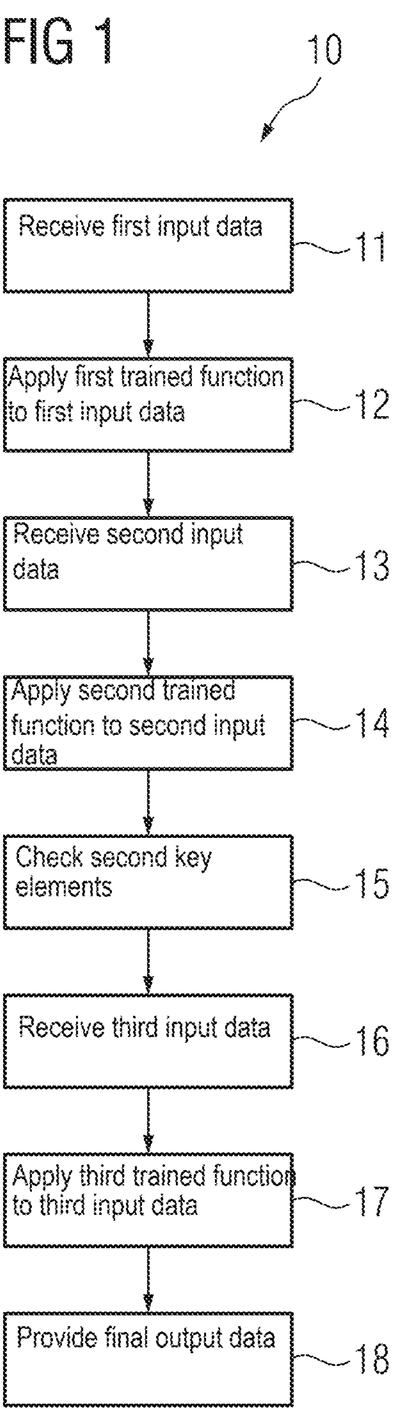
FIG. 1 a schematic representation of the method for providing a complete set of second key elements in an X-ray image according to the present invention in a first embodiment.

FIG. 1 displays an embodiment of method 10 for providing a complete set of second key elements in an X-ray image according to the present invention in a first embodiment.

The computer-implemented method 10 for providing a complete set of second key elements in an X-ray image, comprises the following steps, preferably in the following order:

- receiving 11 first input data, wherein the first input data is an optical image of an examination region,
- applying 12 a first trained function to the first input data, wherein first output data is generated, wherein the first output data comprises detected first key elements and a first collimation region is determined based on the first key elements,
- receiving 13 second input data, wherein the second input data is an X-ray image of an examination region, acquired using the first collimation region,
- applying 14 a second trained function to the second input data (with a computation unit), wherein second output data is generated, wherein the second output data comprises detected second key elements,
- checking 15 a set of second key elements for completeness, in case of an incomplete set of second key elements:
- receiving 16 third input data, wherein the third input data comprises an x-ray image of an examination region acquired using the first collimation region, and the second key elements, applying 17 a third trained function to the third input data, wherein third output data is generated, wherein the third output data comprises at least one estimated third key element to complete the set of second key elements, providing 18 final output data, comprising a complete set of second key elements.

In a preferred embodiment, the complete set of second key elements is transferred to the optical image. A second collimation region is determined based on the transferred complete set of second key elements. A second X-ray image of the examination region is acquired using the second collimation region. A second X-ray image can correspond to the second collimation region.

Figure 2:
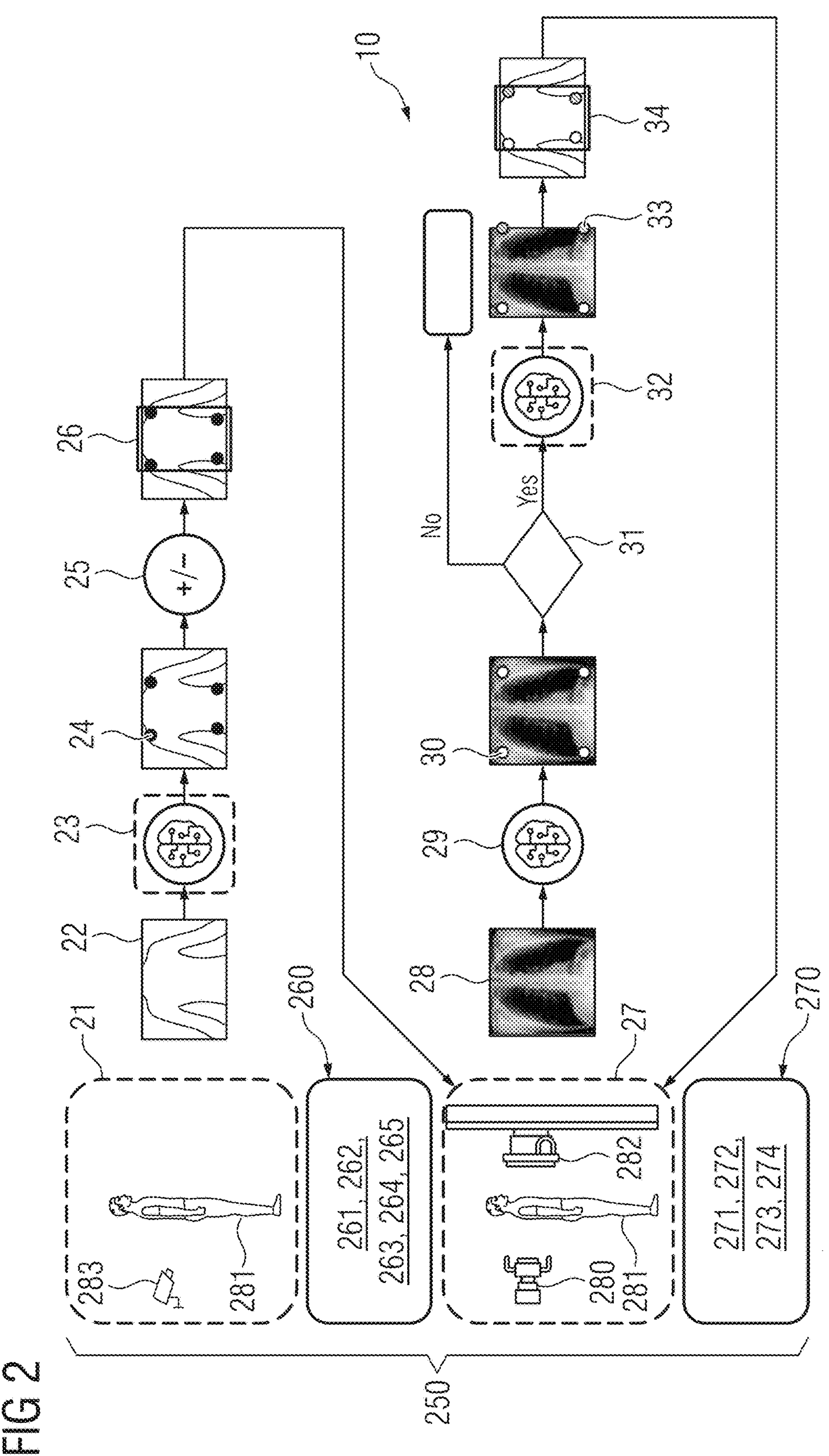
FIG. 2 a schematic representation of the method for providing a complete set of second key elements in an X-ray image according to the present invention in a second embodiment.

FIG. 2 displays an embodiment of the method 10 for providing a complete set of second key elements in an X-ray image according to the present invention in a second embodiment. In step 21, an optical image 22 of the examination region of the patient 281 is acquired by a 3D camera 283. A first trained function 23 determines first key elements 24 in the optical image. Based on the first key elements 24 a collimation region 26 is calculated in step 25.

The collimation region 26 is used to acquire an X-ray image 28 in step 27. The X-ray system comprises an X-ray source 280 and an X-ray detector 282. The patient 281 is located between the X-ray source 280 and the X-ray detector 282. A second trained function 29 is applied to the X-ray image and second key elements 30 are determined.

In step 31, the second key elements 30 are checked, if they form a complete set of second key elements. If at least one second key element is missing, a third trained function 32 is applied to the X-ray image 28 to estimate at least one third key element 33 to complete the set of second key elements. A second collimation region 34 is determined based on the complete set of second key elements including the at least one third key element 33. A second X-ray image is acquired, and the process starts again.

If a complete set of second key elements 30 is found in X-ray image 28, then the X-ray image 28 is complete.

FIG. 2 further displays an embodiment of an X-ray system 250 according to an embodiment of the present invention. The X-ray system 250 comprises the providing system 260. The providing 260 system, comprises: a first interface 261, configured for receiving first input data, wherein the first input data is an optical image of an examination region, a first computation unit 262, configured for applying a first trained function to the first input data, wherein first output data is generated, wherein the first output data comprises detected first key elements, and a first collimation region is determined based on the first key elements, a second interface 263, configured for receiving second input data, wherein the second input data is an X-ray image of an examination region, acquired using the first collimation region, a second computation unit 264, configured for applying a second trained function to the second input data, wherein second output data is generated, wherein the second output data comprises detected second key elements, a checking unit 265, configured for checking a set of second key elements for completeness, in case of an incomplete set of second key elements:

a third interface 266, configured for receiving third input data, wherein the third input data comprises an x-ray image of an examination region acquired using the first collimation region, and the second key elements, a third computation unit 267, configured for applying a third trained function to the third input data, wherein third output data is generated, wherein the third output data comprises at least one estimated third key element to complete the set of second key elements, a fourth interface 268, configured for providing final output data, comprising a complete set of second key elements.

The X-ray system can comprise a training system 270. The training system comprises:

a first training interface 271, configured for receiving input training data, wherein the input training data comprises an X-ray image acquired using the first collimation region, a second training interface 272, configured for receiving output training data, wherein the output training data is related to the input training data, wherein the output training data comprises the at least one third key element, a training computation unit 273, configured for training a third function based on the input training data and the output training data, a third training interface 274, configured for providing the third trained function.

Figure 3:
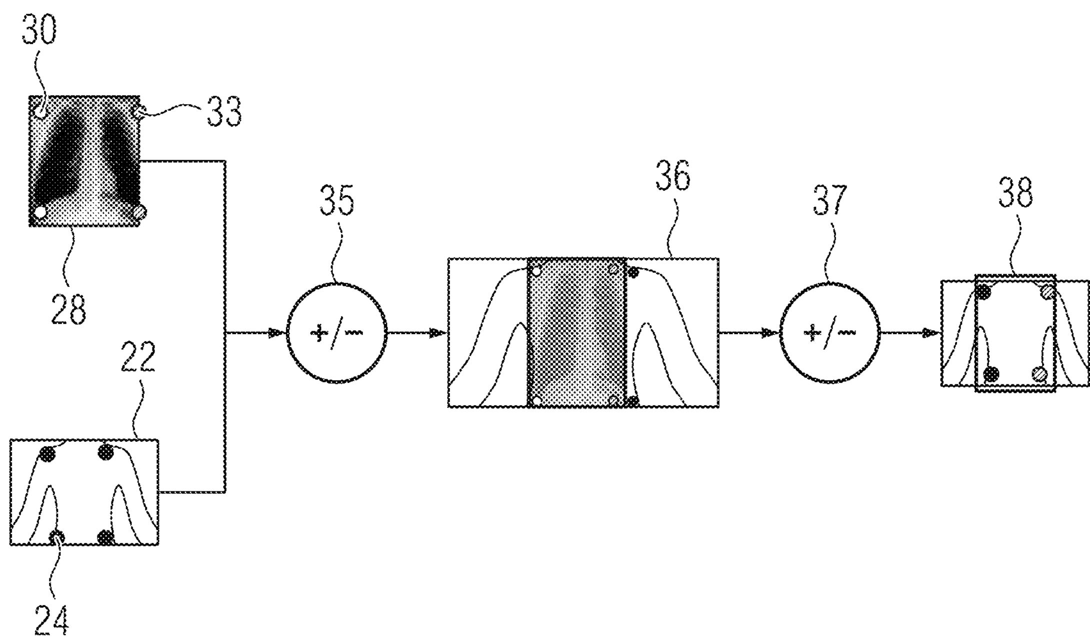
FIG. 3 a schematic representation of the method for mapping second key elements in an X-ray image to an optical image according to an embodiment of the present invention.

FIG. 3 displays an embodiment of method for mapping second key elements in an X-ray image to an optical image according to an embodiment of the present invention. As input, the X-ray image 28 with the second key elements 30 and the at least one third key element 33, and the optical image 22 with the first key elements 24 are used. In step 35, the X-ray image 28 is mapped to the optical image 22 taking in consideration the first key elements 24, the second key elements 30 and the at least one third key element 33. The at least one third key element 33 is mapped to the optical image 36. In a step 37, a second collimation region 38 is calculated.

Figure 4:
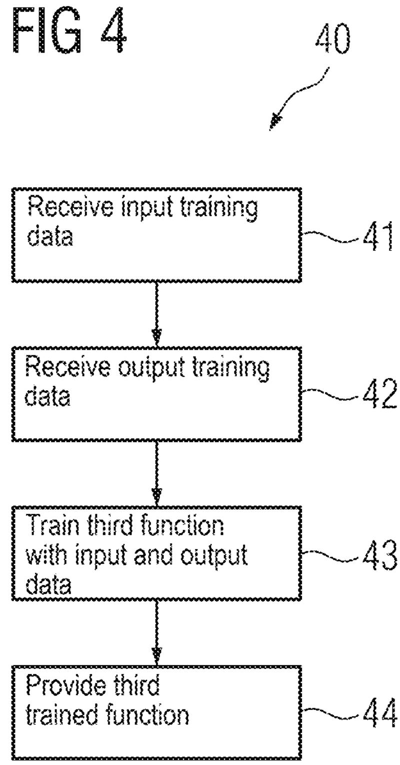
FIG. 4 a schematic representation of the method for providing a trained function according to an embodiment of the present invention.

FIG. 4 displays an embodiment of a computer-implemented method 40 for providing a third trained function, comprising:

receiving 41 input training data, wherein the input training data comprises an X-ray image corresponding to the first collimation region, receiving 42 output training data, wherein the output training data is related to the input training data, wherein the output training data comprises at least one estimated third key element, training 43 a third function based on the input training data and the output training data, providing 44 the third trained function.

Figure 5:
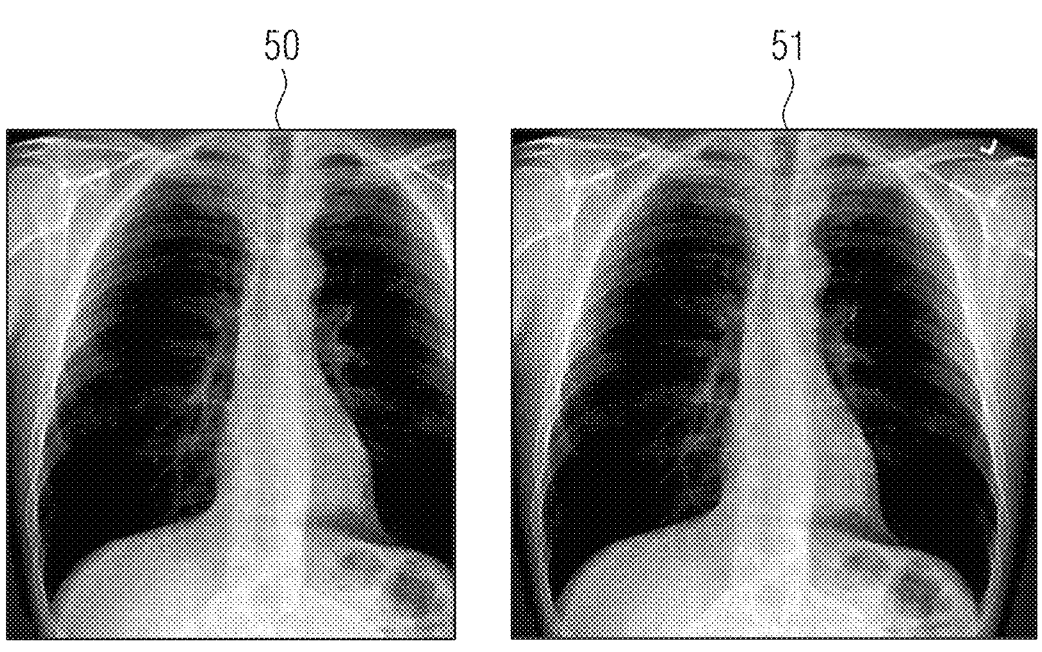
FIG. 5 example X-ray images for use in the method for providing a trained function according to an embodiment of the present invention.

FIG. 5 displays example X-ray images 50, 51 for use in the method for providing a trained function according to an embodiment of the present invention. The at least one estimated third key element is deduced from a complete X-ray image 51. The second collimation region is determined by the outline of the complete X-ray image 51. The input training data is based on a cropped X-ray image 50 of the complete X-ray image 51. The collimation region is determined by the outline of the cropped X-ray image 50.

The example of chest x-ray image is considered to explain embodiments of the present invention. However, embodiments of the present invention can be applied to other body parts as well. The cropped X-ray image 50 is an example of a bad collimation region for acquiring a chest X-ray image, as it can be seen lower part of left lung is missing in the cropped X-ray image 50 due to incorrect collimator parameters. The complete X-ray image 51 shows the whole lung.

Figure 6:
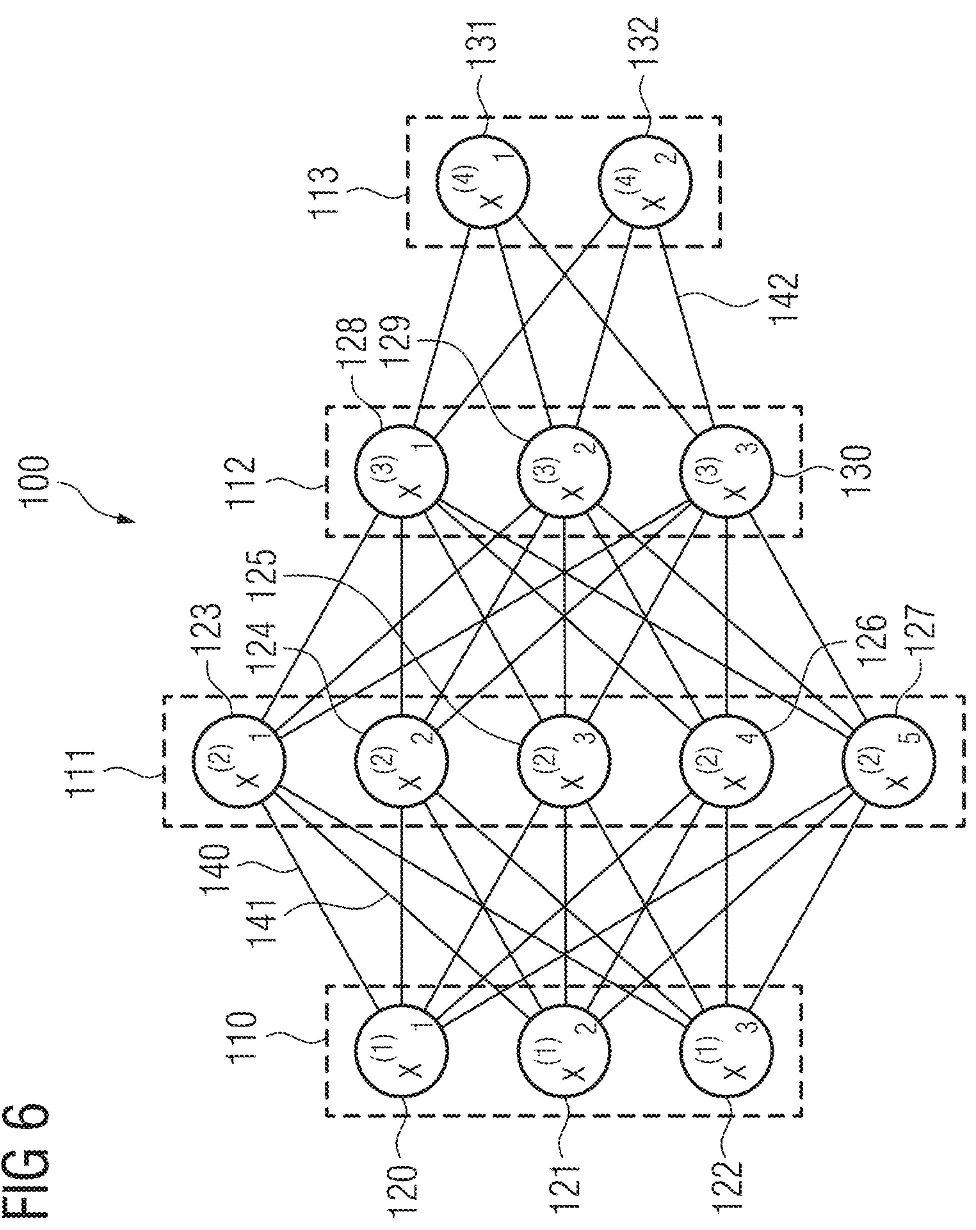
FIG. 6 a schematic representation of a neural network according to an embodiment of the present invention.

FIG. 6 displays an embodiment of an artificial neural network 100. Alternative terms for "artificial neural network" are "neural network", "artificial neural net" or "neural net".

The artificial neural network 100 comprises nodes 120, 132 and edges 140, . . . , 142, wherein each edge 140, . . . , 142 is a directed connection from a first node 120, . . . , 132 to a second node 120, . . . , 132. In general, the first node 120, . . . , 132 and the second node 120, . . . , 132 are different nodes 120, 132, it is also possible that the first node 120, . . . , 132 and the second node 120, . . . , 132 are identical. For example, in FIG. 1 the edge 140 is a directed connection from the node 120 to the node 123, and the edge 142 is a directed connection from the node 130 to the node 132. An edge 140, . . . , 142 from a first node 120, . . . , 132 to a second node 120, . . . , 132 is also denoted as "ingoing edge" for the second node 120, . . . , 132 and as "outgoing edge" for the first node 120, . . . , 132.

In this embodiment, the nodes 120, . . . , 132 of the artificial neural network 100 can be arranged in layers 110, . . . , 113, wherein the layers can comprise an intrinsic order introduced by the edges 140, . . . , 142 between the nodes 120, . . . , 132. In particular, edges 140, . . . , 142 can exist only between neighboring layers of nodes. In the displayed embodiment, there is an input layer 110 comprising only nodes 120, . . . , 122 without an incoming edge, an output layer 113 comprising only nodes 131, 132 without outgoing edges, and hidden layers 111, 112 in-between the input layer 110 and the output layer 113. In general, the number of hidden layers 111, 112 can be chosen arbitrarily. The number of nodes 120, . . . , 122 within the input layer 110 usually relates to the number of input values of the neural network, and the number of nodes 131, 132 within the output layer 113 usually relates to the number of output values of the neural network.

In particular, a (real) number can be assigned as a value to every node 120, . . . , 132 of the neural network 100. Here, x(n)i denotes the value of the i-th node 120, . . . , 132 of the n-th layer 110, . . . , 113. The values of the nodes 120, . . . , 122 of the input layer 110 are equivalent to the input values of the neural network 100, the values of the nodes 131, 132 of the output layer 113 are equivalent to the output value of the neural network 100. Furthermore, each edge 140, . . . , 142 can comprise a weight being a real number, in particular, the weight is a real number within the interval [−1, 1] or within the interval [0, 1]. Here, w(m,n)i,j denotes the weight of the edge between the i-th node 120, . . . , 132 of the m-th layer 110, . . . , 113 and the j-th node 120, . . . , 132 of the n-th layer 110, . . . , 113. Furthermore, the abbreviation w(n)i,j is defined for the weight w(n,n+1)i,j.

In particular, to calculate the output values of the neural network 100, the input values are propagated through the neural network. In particular, the values of the nodes 120, . . . , 132 of the (n+1)-th layer 110, . . . , 113 can be calculated based on the values of the nodes 120, . . . , 132 of the n-th layer 110, 113 by $$x_j^{(n+1)} = f\left(\sum_i x_i^{(n)} \cdot w_{i,j}^{(n)}\right).$$

Herein, the function f is a transfer function (another term is "activation function"). Known transfer functions are step functions, sigmoid function (e.g. the logistic function, the generalized logistic function, the hyperbolic tangent, the Arctangent function, the error function, the smoothstep function) or rectifier functions. The transfer function is mainly used for normalization purposes.

In particular, the values are propagated layer-wise through the neural network, wherein values of the input layer 110 are given by the input of the neural network 100, wherein values of the first hidden layer 111 can be calculated based on the values of the input layer 110 of the neural network, wherein values of the second hidden layer 112 can be calculated based in the values of the first hidden layer 111, etc.

In order to set the values w(m,n)i,j for the edges, the neural network 100 has to be trained using training data. In particular, training data comprises training input data and training output data (denoted as ti). For a training step, the neural network 100 is applied to the training input data to generate calculated output data. In particular, the training data and the calculated output data comprise a number of values, said number being equal with the number of nodes of the output layer.

In particular, a comparison between the calculated output data and the training data is used to recursively adapt the weights within the neural network 100 (backpropagation algorithm). In particular, the weights are changed according to $$w'^{(n)}_{i,j} = w^{(n)}_{i,j} - \gamma \cdot \delta^{(n)}_j \cdot x^{(n)}_i$$

wherein γ is a learning rate, and the numbers δ(n)j can be recursively calculated as $$\delta_j^{(n)} = \left(\sum_k \delta_k^{(n+1)} \cdot w_{j,k}^{(n+1)}\right) \cdot f'\left(\sum_i x_i^{(n)} \cdot w_{i,j}^{(n)}\right)$$

based on δ(n+1)j, if the (n+1)-th layer is not the output layer, and $$\delta_j^{(n)} = \left(x_k^{(n+1)} - t_j^{(n+1)}\right) \cdot f'\left(\sum_i x_i^{(n)} \cdot w_{i,j}^{(n)}\right)$$

if the (n+1)-th layer is the output layer 113, wherein f' is the first derivative of the activation function, and y(n+1)j is the comparison training value for the j-th node of the output layer 113.

Figure 7:
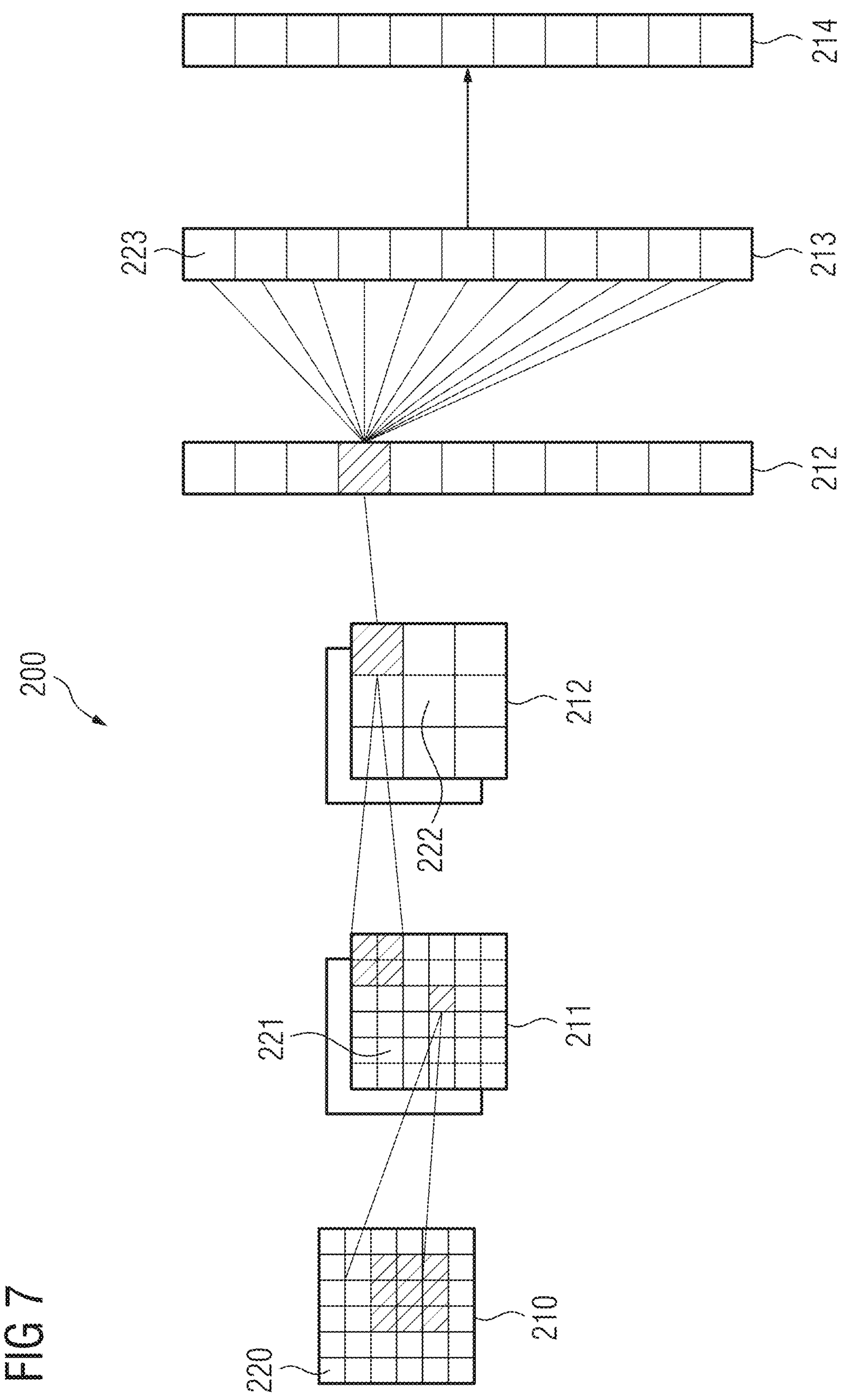
FIG. 7 a schematic representation of a convolutional neural network according to an embodiment of the present invention.

FIG. 7 displays an embodiment of a convolutional neural network 200. In the displayed embodiment, the convolutional neural network comprises 200 an input layer 210, a convolutional layer 211, a pooling layer 212, a fully connected layer 213 and an output layer 214. Alternatively, the convolutional neural network 200 can comprise several convolutional layers 211, several pooling layers 212 and several fully connected layers 213, as well as other types of layers. The order of the layers can be chosen arbitrarily, usually fully connected layers 213 are used as the last layers before the output layer 214.

In particular, within a convolutional neural network 200 the nodes 220, . . . , 224 of one layer 210, . . . , 214 can be considered to be arranged as a d-dimensional matrix or as a d-dimensional image. In particular, in the two-dimensional case the value of the node 220, . . . , 224 indexed with i and j in the n-th layer 210, . . . , 214 can be denoted as x(n)[i,j]. However, the arrangement of the nodes 220, . . . , 224 of one layer 210, . . . , 214 does not have an effect on the calculations executed within the convolutional neural network 200 as such, since these are given solely by the structure and the weights of the edges.

In particular, a convolutional layer 211 is characterized by the structure and the weights of the incoming edges forming a convolution operation based on a certain number of kernels. In particular, the structure and the weights of the incoming edges are chosen such that the values x(n)k of the nodes 221 of the convolutional layer 211 are calculated as a convolution x(n)k=Kk*x(n−1) based on the values x(n−1) of the nodes 220 of the preceding layer 210, where the convolution * is defined in the two-dimensional case as $$x_k^{(n)}[i, j] = (K_k * x^{(n-1)})[i, j] = \sum_{i'} \sum_{j'} K_k[i', j'] \cdot x^{(n-1)}[i - i', j - j'].$$

Here the k-th kernel Kk is a d-dimensional matrix (in this embodiment a two-dimensional matrix), which is usually small compared to the number of nodes 220, . . . , 224 (e.g. a 3×3 matrix, or a 5×5 matrix). In particular, this implies that the weights of the incoming edges are not independent, but chosen such that they produce said convolution equation. In particular, for a kernel being a 3×3 matrix, there are only 9 independent weights (each entry of the kernel matrix corresponding to one independent weight), irrespectively of the number of nodes 220, . . . , 224 in the respective layer 210, . . . , 214. In particular, for a convolutional layer 211 the number of nodes 221 in the convolutional layer is equivalent to the number of nodes 220 in the preceding layer 210 multiplied with the number of kernels.

If the nodes 220 of the preceding layer 210 are arranged as a d-dimensional matrix, using a plurality of kernels can be interpreted as adding a further dimension (denoted as "depth" dimension), so that the nodes 221 of the convolutional layer 221 are arranged as a (d+1)-dimensional matrix. If the nodes 220 of the preceding layer 210 are already arranged as a (d+1)-dimensional matrix comprising a depth dimension, using a plurality of kernels can be interpreted as expanding along the depth dimension, so that the nodes 221 of the convolutional layer 221 are arranged also as a (d+1)-dimensional matrix, wherein the size of the (d+1)-dimensional matrix with respect to the depth dimension is by a factor of the number of kernels larger than in the preceding layer 210.

The advantage of using convolutional layers 211 is that spatially local correlation of the input data can exploited by enforcing a local connectivity pattern between nodes of adjacent layers, in particular by each node being connected to only a small region of the nodes of the preceding layer.

In the displayed embodiment, the input layer 210 comprises 36 nodes 220, arranged as a two-dimensional 6×6 matrix. The convolutional layer 211 comprises 72 nodes 221, arranged as two two-dimensional 6×6 matrices, each of the two matrices being the result of a convolution of the values of the input layer with a kernel. Equivalently, the nodes 221 of the convolutional layer 211 can be interpreted as arranges as a three-dimensional 6×6×2 matrix, wherein the last dimension is the depth dimension.

A pooling layer 212 can be characterized by the structure and the weights of the incoming edges and the activation function of its nodes 222 forming a pooling operation based on a non-linear pooling function f. For example, in the two dimensional case the values x(n) of the nodes 222 of the pooling layer 212 can be calculated based on the values x(n−1) of the nodes 221 of the preceding layer 211 as $$x^{(n)}[i,j]=f(x^{(n-1)}[id_1,jd_2], \ldots ,x^{(n-1)}[id_1+d_1-1,jd_2+d_2-1])$$

In other words, by using a pooling layer 212 the number of nodes 221, 222 can be reduced, by replacing a number d1·d2 of neighboring nodes 221 in the preceding layer 211 with a single node 222 being calculated as a function of the values of said number of neighboring nodes in the pooling layer. In particular, the pooling function f can be the max-function, the average or the L2-Norm. In particular, for a pooling layer 212 the weights of the incoming edges are fixed and are not modified by training.

The advantage of using a pooling layer 212 is that the number of nodes 221, 222 and the number of parameters is reduced. This leads to the amount of computation in the network being reduced and to a control of overfitting.

In the displayed embodiment, the pooling layer 212 is a max-pooling, replacing four neighboring nodes with only one node, the value being the maximum of the values of the four neighboring nodes. The max-pooling is applied to each d-dimensional matrix of the previous layer; in this embodiment, the max-pooling is applied to each of the two two-dimensional matrices, reducing the number of nodes from 72 to 18.

A fully-connected layer 213 can be characterized by the fact that a majority, in particular, all edges between nodes 222 of the previous layer 212 and the nodes 223 of the fully-connected layer 213 are present, and wherein the weight of each of the edges can be adjusted individually.

In this embodiment, the nodes 222 of the preceding layer 212 of the fully-connected layer 213 are displayed both as two-dimensional matrices, and additionally as non-related nodes (indicated as a line of nodes, wherein the number of nodes was reduced for a better presentability). In this embodiment, the number of nodes 223 in the fully connected layer 213 is equal to the number of nodes 222 in the preceding layer 212. Alternatively, the number of nodes 222, 223 can differ.

Furthermore, in this embodiment the values of the nodes 224 of the output layer 214 are determined by applying the Softmax function onto the values of the nodes 223 of the preceding layer 213. By applying the Softmax function, the sum of the values of all nodes 224 of the output layer is 1, and all values of all nodes 224 of the output layer are real numbers between 0 and 1. In particular, if using the convolutional neural network 200 for categorizing input data, the values of the output layer can be interpreted as the probability of the input data falling into one of the different categories.

A convolutional neural network 200 can also comprise a ReLU (acronym for "rectified linear units") layer. In particular, the number of nodes and the structure of the nodes contained in a ReLU layer is equivalent to the number of nodes and the structure of the nodes contained in the preceding layer. In particular, the value of each node in the ReLU layer is calculated by applying a rectifying function to the value of the corresponding node of the preceding layer. Examples for rectifying functions are f(x)=max(0,x), the tangent hyperbolics function or the sigmoid function.

In particular, convolutional neural networks 200 can be trained based on the backpropagation algorithm. For preventing overfitting, methods of regularization can be used, e.g. dropout of nodes 220, . . . , 224, stochastic pooling, use of artificial data, weight decay based on the L1 or the L2 norm, or max norm constraints.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

In addition, or alternative, to that discussed above, units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Although the present invention has been further illustrated in detail by embodiments thereof, the present invention is not limited by the disclosed examples and other variations may be derived therefrom by those skilled in the art without departing from the scope of protection of the present invention.

What is claimed is:

1. A computer-implemented method for providing a complete set of second key elements in an X-ray image, the computer-implemented method comprising:

receiving first input data, wherein the first input data is an optical image of an examination region of a patient;

applying a first trained function to the first input data to generate first output data, wherein the first output data includes detected first key elements, and wherein a first collimation region is determined based on the detected first key elements;

receiving second input data, wherein the second input data is an X-ray image of the examination region, and the X-ray image of the examination region is acquired using the first collimation region;

applying a second trained function to the second input data to generate second output data, wherein the second output data includes detected second key elements;

checking a set of second key elements for completeness;

receiving third input data in response to the set of second key elements being incomplete, wherein the third input data includes the second key elements and the X-ray image of the examination region acquired using the first collimation region;

applying a third trained function to the third input data to generate third output data, wherein the third output data includes at least one estimated third key element to complete the set of second key elements; and providing final output data including a complete set of second key elements, wherein the complete set of second key elements is transferred to the optical image.

2. The computer-implemented method according to claim 1, wherein a second collimation region is determined based on the complete set of second key elements.

3. The computer-implemented method according to claim 2, wherein another X-ray image of the examination region is acquired using the second collimation region.

4. A computer-implemented method for providing a trained function, the computer-implemented method comprising:

receiving input training data, wherein the input training data includes an X-ray image corresponding to a first collimation region, the input training data is based on a cropped X-ray image, the cropped X-ray image is determined based on a complete X-ray image, and the cropped X-ray image is an example of a bad collimation;

receiving output training data, wherein the output training data is related to the input training data, and wherein the output training data includes at least one estimated key element;

training a function based on the input training data and the output training data to obtain the trained function; and providing the trained function.

5. The computer-implemented method according to claim 4, wherein the at least one estimated key element is deduced from the complete X-ray image.

6. The computer-implemented method according to claim 1, further comprising:

receiving input training data, wherein the input training data includes an X-ray image corresponding to the first collimation region;

receiving output training data, wherein the output training data is related to the input training data, and wherein the output training data includes the at least one estimated third key element; and obtaining the third trained function by training a function based on the input training data and the output training data.

7. A providing system, comprising:

a first interface, configured to receive first input data, wherein the first input data is an optical image of an examination region of a patient;

a first computation unit, configured to apply a first trained function to the first input data to generate first output data, wherein the first output data includes detected first key elements, and a first collimation region is determined based on the detected first key elements;

a second interface, configured to receive second input data, wherein the second input data is an X-ray image of the examination region acquired using the first collimation region;

a second computation unit, configured to apply a second trained function to the second input data to generate second output data, wherein the second output data includes detected second key elements;

a checking unit, configured to check a set of second key elements for completeness;

a third interface, configured to receive third input data in response to the set of second key elements being incomplete, wherein the third input data includes the second key elements and the X-ray image of the examination region acquired using the first collimation region;

a third computation unit, configured to apply a third trained function to the third input data to generate third output data, wherein the third output data includes at least one estimated third key element to complete the set of second key elements; and a fourth interface, configured to provide final output data including a complete set of second key elements, wherein the complete set of second key elements is transferred to the optical image.

8. A non-transitory computer-readable medium comprising instructions that, when executed by a providing system, cause the providing system to carry out the computer-implemented method of claim 1.

9. A training system, comprising a first training interface, configured to receive input training data, wherein the input training data includes an X-ray image corresponding to a first collimation region, the input training data is based on a cropped X-ray image, and the cropped X-ray image is an example of a bad collimation;

a second training interface, configured to receive output training data, wherein the output training data is related to the input training data, and wherein the output training data includes at least one estimated key element;

a training computation unit, configured to train a function based on the input training data and the output training data to obtain a trained function; and a third training interface, configured to provide the trained function.

10. A non-transitory computer-readable medium comprising instructions that, when executed by a training system, cause the training system to carry out the computer-implemented method of claim 4.

11. An X-ray system comprising the providing system according to claim 7.

12. The computer-implemented method according to claim 2, further comprising:

receiving input training data, wherein the input training data includes an X-ray image corresponding to the first collimation region;

receiving output training data, wherein the output training data is related to the input training data, and wherein the output training data includes the at least one estimated third key element; and obtaining the third trained function by training a function based on the input training data and the output training data.

13. The computer-implemented method according to claim 3, further comprising:

receiving input training data, wherein the input training data includes an X-ray image corresponding to the first collimation region;

receiving output training data, wherein the output training data is related to the input training data, and wherein the output training data includes the at least one estimated third key element; and obtaining the third trained function by training a function based on the input training data and the output training data.

14. A providing system, comprising:

at least one interface configured to receive first input data, wherein the first input data is an optical image of an examination region of a patient, receive second input data, wherein the second input data is an X-ray image of the examination region acquired using a first collimation region, receive third input data in response to a set of second key elements being incomplete, wherein the third input data includes detected second key elements and the X-ray image of the examination region acquired using the first collimation region, and provide final output data including a complete set of second key elements; and at least one processor configured to execute computer-readable instructions to cause the providing system to apply a first trained function to the first input data to generate first output data, wherein the first output data includes detected first key elements, and the first collimation region is determined based on the detected first key elements, apply a second trained function to the second input data to generate second output data, wherein the second output data includes the detected second key elements, check the set of second key elements for completeness, and apply a third trained function to the third input data to generate third output data, wherein the third output data includes at least one estimated third key element to complete the set of second key elements, wherein the complete set of second key elements is transferred to the optical image.

15. The providing system according to claim 14, wherein the at least one processor is configured to execute the computer-readable instructions to cause the providing system to transfer the complete set of second key elements to the optical image.

* * * * *